US010934516B2

United States Patent
Arnold et al.

(10) Patent No.: US 10,934,516 B2
(45) Date of Patent: Mar. 2, 2021

(54) METHOD FOR CONTROLLED OPERATION OF A BIOTECHNOLOGICAL APPARATUS AND BIOREACTOR SYSTEM

(71) Applicant: DASGIP INFORMATION AND TECHNOLOGY GMBH, Julich (DE)

(72) Inventors: Matthias Arnold, Aachen (DE); Guido Ertel, Dormagen (DE); Sebastian Selzer, Aachen (DE)

(73) Assignee: DASGIP Information and Technology GmbH, Julich (DE)

( * ) Notice: Subject to any disclaimer, the term of this patent is extended or adjusted under 35 U.S.C. 154(b) by 745 days.

(21) Appl. No.: 15/659,236

(22) Filed: Jul. 25, 2017

(65) Prior Publication Data

US 2018/0010083 A1    Jan. 11, 2018

Related U.S. Application Data

(62) Division of application No. 14/351,054, filed as application No. PCT/EP2012/070094 on Oct. 10, 2012, now Pat. No. 9,745,547.

(30) Foreign Application Priority Data

Oct. 10, 2011 (DE) .................. 10 2011 054 363
Oct. 10, 2011 (DE) .................. 10 2011 054 365

(51) Int. Cl.
*C12M 1/34* (2006.01)
*C12M 1/36* (2006.01)
*H02J 3/14* (2006.01)

(52) U.S. Cl.
CPC ............ *C12M 41/12* (2013.01); *C12M 41/48* (2013.01); *H02J 3/14* (2013.01)

(58) Field of Classification Search
CPC .......... C12M 41/48; C12M 41/12; H02J 3/14; Y10T 307/406
See application file for complete search history.

(56) References Cited

U.S. PATENT DOCUMENTS

| 4,957,512 A | 9/1990 | Denisov et al. |
| 6,202,713 B1 | 3/2001 | Drescher et al. |

(Continued)

FOREIGN PATENT DOCUMENTS

| CN | 1619941 A | 5/2005 |
| CN | 201149352 | 11/2008 |

(Continued)

OTHER PUBLICATIONS

International Preliminary Report on Patentability from International Application No. PCT/EP2012/070094 dated Apr. 24, 2014.

(Continued)

*Primary Examiner* — Shogo Sasaki
(74) *Attorney, Agent, or Firm* — Merchant & Gould P.C.

(57) ABSTRACT

A method for controlling electrical power consumption for a first group of functional which can be used for operational management during operation of the bioreactor components during operation comprises, inter alia, adjusting a present power control signal for one or more of the functional components from the first group in order to optimise power consumption, when a comparison shows for the first group of functional components that the currently required total electrical power consumption is greater than a predefined total electrical power consumption, such that, for the first group of functional components, an adjusted total electrical power consumption is not greater than the predefined total electrical power consumption. A biotechnological apparatus comprises a bioreactor, a reactor vessel formed in the bioreactor and having a cultivation chamber, and a tempera- (Continued)

Figure 1:
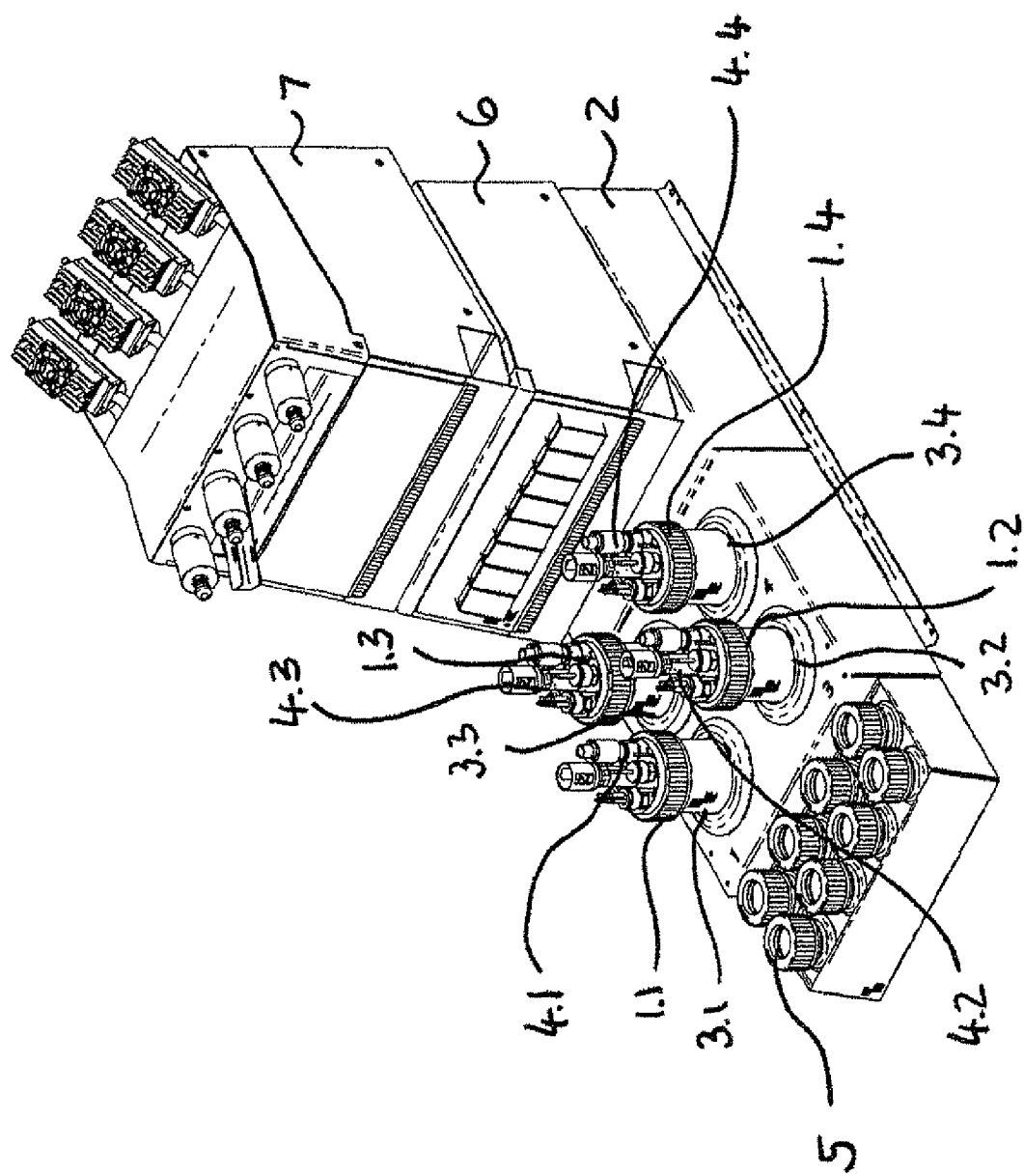

ture control device provided with a heat pump and configured to control the temperature of the cultivation chamber.

12 Claims, 6 Drawing Sheets

(56) References Cited

U.S. PATENT DOCUMENTS

| | | | |
|---|---|---|---|
| 7,467,306 | B2 | 12/2008 | Cartes et al. |
| 7,489,988 | B2 | 2/2009 | Matsui et al. |
| 7,831,843 | B2 | 11/2010 | Brundridge et al. |
| 7,996,690 | B2 | 8/2011 | Shetty et al. |
| 8,522,996 | B2 | 9/2013 | Beese et al. |
| 2001/0050276 | A1 | 12/2001 | Inami |
| 2003/0056720 | A1 | 3/2003 | Dauelsberg et al. |
| 2003/0119201 | A1 | 6/2003 | Wolfram et al. |
| 2004/0029170 | A1 | 2/2004 | Wolfram et al. |
| 2004/0248077 | A1* | 12/2004 | Rodriguez Rilo ..... C12M 29/18 435/4 |
| 2004/0254654 | A1 | 12/2004 | Donnelly et al. |
| 2005/0106742 | A1* | 5/2005 | Wahl ................ B01L 3/502792 436/149 |
| 2005/0107892 | A1 | 5/2005 | Matsui et al. |
| 2005/0239119 | A1* | 10/2005 | Tsukada ................ C12Q 1/686 435/6.12 |
| 2005/0282266 | A1* | 12/2005 | Teng .......................... B01L 7/52 435/286.1 |
| 2008/0057934 | A1 | 3/2008 | Sung et al. |
| 2008/0139865 | A1 | 6/2008 | Galliher et al. |
| 2008/0155284 | A1 | 6/2008 | Shimohata et al. |
| 2009/0077407 | A1 | 3/2009 | Akimoto |
| 2009/0152744 | A1 | 6/2009 | Mou |
| 2010/0211807 | A1 | 8/2010 | Akimoto |
| 2010/0316446 | A1 | 12/2010 | Runyon |
| 2014/0247157 | A1 | 9/2014 | Ikeya et al. |

FOREIGN PATENT DOCUMENTS

| | | |
|---|---|---|
| CN | 101974415 A | 2/2011 |
| DE | 3927701 A1 | 2/1991 |
| DE | 3924701 A1 | 10/1991 |
| DE | 19932833 A1 | 1/2001 |
| DE | 10120056 A1 | 12/2001 |
| DE | 202006008928 U1 | 8/2006 |
| DE | 10 2009 039 535 A1 | 3/2011 |
| DE | 102009039535 A1 | 3/2011 |
| EP | 0053383 A1 | 6/1982 |
| EP | 0156176 A1 | 10/1985 |
| EP | 1533893 A2 | 5/2005 |
| GB | 2003596 A | 3/1979 |
| JP | 54-037958 A | 3/1979 |
| JP | 60-203180 A | 10/1985 |
| JP | S61-285361 A | 12/1986 |
| JP | 4-168920 A | 6/1992 |
| JP | 05-68344 A | 3/1993 |
| JP | 05-251595 A | 9/1993 |
| JP | 2000-324722 A | 11/2000 |
| JP | 2003-525349 A | 8/2003 |
| JP | 2005-020966 A | 1/2005 |
| JP | 2005-176592 A | 6/2005 |
| JP | 2008-061250 A | 3/2008 |
| JP | 2008-160971 A | 7/2008 |
| JP | 2009-116225 A | 5/2009 |
| JP | 2009-543553 A | 12/2009 |
| JP | 2010-158185 A | 7/2010 |
| JP | 2010-200249 A | 9/2010 |
| JP | 2011-519115 A | 6/2011 |
| WO | 9902961 A1 | 1/1999 |
| WO | 2005095576 A2 | 10/2005 |
| WO | 2006086547 A2 | 8/2006 |
| WO | 2006102890 A1 | 10/2006 |
| WO | 2008088379 A2 | 7/2008 |
| WO | 2009099486 A1 | 8/2009 |
| WO | 2013053778 A1 | 4/2013 |
| WO | 2013053779 A1 | 4/2013 |
| WO | 2013150064 A1 | 10/2013 |
| WO | 2013186294 A1 | 12/2013 |

OTHER PUBLICATIONS

Chinese Search Report for Chinese Patent Application No. 201280060915.0, dated Jul. 23, 2015.
Chinese Office Action for Chinese Patent Application No. 201280060915.0, dated Jul. 31, 2015.
Japanese Office Action for Japanese Patent Application No. 2014-535056, dated Aug. 27, 2015.
Examination Report from Related Japanese Patent Application No. 2014-535056, dated Jun. 7, 2016, 5 pages.
Notice of Rejection from corresponding Japanese Patent Application No. 2016-013460, dated Feb. 7, 2017.
Communication pursuant to Article 94(3) EBC (Office Action) issued in corresponding European Patent Application No. 12772921.8, dated Mar. 21, 2018 (8 pages).
International Search Report and Written Opinion from International Application No. PCT/EP2012/070094 dated Dec. 3, 2012.

* cited by examiner

METHOD FOR CONTROLLED OPERATION OF A BIOTECHNOLOGICAL APPARATUS AND BIOREACTOR SYSTEM

This application is a Divisional Application of U.S. patent application Ser. No. 14/351,054, filed 10 Apr. 2014, which is a National Stage Application of PCT/EP2012/070094, filed 10 Oct. 2012, which claims benefit of Serial No. 10 2011 054 363.5, filed 10 Oct. 2011 in Germany and which claims benefit of Serial No. 10 2011 054 365.1, filed 10 Oct. 2011 in Germany, and the entire disclosures of these applications are incorporated herein by reference. To the extent appropriate, a claim of priority is made to each of the above disclosed applications.

The invention relates to a method for controlled operation of a biotechnological apparatus and to a biotechnological apparatus.

The invention further relates to the field of controlling the temperature of one or more cultivation chambers provided in a reactor vessel of a bioreactor in a biotechnological apparatus.

BACKGROUND OF THE INVENTION

Bioreactors, also referred to as fermenters, are a part of biotechnological apparatuses. They have a closed reaction chamber, in which eukaryotic or prokaryotic cells are cultivated under conditions that are as optimal, defined and controlled as possible. Conversions of substances, mostly automated and controlled by process engineering, are researched, optimised and performed using the boundary conditions necessary for the organism and in the presence of the primary and secondary substances required for the process.

In typical biotechnological methods carried out on "benchtop scale" (laboratory scale), glass reactor vessels are frequently used. This allows an autoclavable bioreactor to be designed in which the glass reactor vessel can be steam sterilised in one piece in an autoclave. It is then necessary in such cases to separate the connections for the entire reactor vessel from the control units before autoclaving. Connections are typically in the form of hose connectors such as clamp screw connections, push-in connectors, crimp connections or the like. Such an autoclavable design of the bioreactor thus requires that functional components of the biotechnological apparatus which connect to the bioreactor itself are mounted on the reactor vessel as efficiently as possible and can be dismantled again when autoclaving is due.

Another bioreactor design takes the form of single-use bioreactors, in which the reactor vessel, for example, is used in one cultivation process only, whereas functional elements assigned to the reactor vessel, such as stirrer drives, or the temperature control unit for exhaust gas removal and/or cultivation chamber, can be reused. In this connection also, it is necessary that functional components of the biotechnological apparatus which are coupled to the bioreactor be mounted on the reactor vessel and dismantled again after use as efficiently as possible.

Bioreactors are usually operated in a temperature range of about 10° C. to about 50° C., due to the characteristics of the biological cultures used therein, and also, in rather rare cases of extremophile cultures, at temperatures between −20 and 150° C. Various methods and devices have been proposed for controlling the temperature of cultures. One method involves directly heating the exterior of the reactor vessel with the aid of thermally coupled electrical heating elements, using heating blankets or temperature-control jaws containing integrated elements, for example. Cooling is effected using immersed heat exchangers, such as cooling fingers or cooling coils through which a coolant flows.

In connection with the aforementioned heating, the exterior of the reactor vessel can be cooled, alternatively, by means of a thermally coupled device, typically of a jaw-like or pot-like design, the temperature of which can be lowered by a coolant passed through it with a controllable volumetric flow rate.

One known alternative is to use double-walled reactor vessels, with a pre-heated or pre-cooled fluid flowing through the outer compartment separated from the interior of the reactor vessel. The fluid is typically heated in a cycle with integrated heating, for example by means of an electrical heater. The fluid is cooled by means of a secondary coolant in the heat exchanger or by replacement, i.e. by mixing additional coolant to the cycle and simultaneously removing the same amount of warm fluid.

Another known alternative, finally, is to use indirect external heating in the form of radiant heat, for example an infrared source. Cooling is then performed in a manner as described above.

A control loop for controlling the temperature of the cultivation chamber in the bioreactor is typically formed by a temperature sensor, appropriately immersed into the culture in the cultivation chamber, and a temperature controller. In rare cases, the supply temperature is also controlled.

For small, parallel cultures, several miniaturised reactor vessels, such as multi-well plates or shake flasks, are arranged in temperature-controlled compartments, for example incubators or thermal chambers. In these cases, only the temperature of the gas, for example a mixture of N2, O2 and CO2, is suitably controlled in the compartment, typically. The temperature of the culture is not measured directly or by feedback, typically, which can lead to undefined temperatures within the culture, particularly in the case of cultures with a high cell density and strong specific biological heat production.

In research and development, autoclavable bioreactor systems that are not fixedly installed are frequently used. In such systems, the reactor or culture vessel is temporarily separated, for sterilisation purposes, from those system components that cannot be steam sterilised. This involves additional handling in the case of known methods and devices for controlling temperature. It is necessary to cut the fluid circulation, which means that appropriate coupling and shut-off devices must be provided. Depending on the fluid used for temperature control, the latter must also be removed from the subsystem to be sterilised. Another disadvantage of fluid-operated cooling devices in many cases is the strong formation of condensate (from ambient air) on system components, for example on connection tubes or the like. Analogous disadvantages ensue from connecting and disconnecting temperature-control elements in single-use bioreactors.

Since the heat capacity of the (mostly aqueous) temperature-control fluid is relatively high, it cannot be conditioned (cooled) in the short term when this is necessary, but must typically be kept permanently available in suitable form. In addition to the frequently very poor energy efficiency of the devices used for this purpose, such as recirculating coolers and/or poorly insulated conduits, this often causes an additional nuisance in the form of noise and heat in the workplace.

In most cases, the electrical heater is operated with primary grid voltage. One disadvantage of this is that electrical safety must be ensured by means of appropriate insulation, which involves additional expense in the case of autoclavable bioreactors that are not fixedly installed. There is also the economic disadvantage that suitable heating elements with different operating voltages must be provided for every market that is targeted.

Another specific disadvantage of all the known systems is their poor energy efficiency, particularly in cooling mode.

Regarding control systems, EP 1 533 893 A2 discloses a generator control system. In the case where a user changes a set state of apparatuses, an apparatus operation control portion repressively controls the apparatuses, in spite of an instruction of a control signal according to that change, so that an increasing amount of power consumption of the apparatuses obtained from an apparatus power consumption measuring portion will not exceed an increasing amount of the generating capacity of a generator obtained from a generating capacity measuring portion so as to gradually bring it closer to a target set state set up by the user. However, further improvements are sought.

SUMMARY OF THE INVENTION

The object of the invention is to specify an improved technology in the field of controlled operation of a biotechnological apparatus comprising one or more bioreactors, with which the device can be operated more efficiently in several respects, in particular with regard to energy-efficient operation that is gentle on the reactor vessel.

A further object of the invention is to specify improved technologies in the field of temperature control of one or more cultivation chambers each formed in a bioreactor in a biotechnological apparatus, with which the temperature of the cultivation system can be efficiently controlled.

This object is achieved, according to the invention, by a method according to independent claim 1 for controlled operation of a biotechnological apparatus and by a biotechnological apparatus according to independent claim 13. Advantageous embodiments of the invention are described in the dependent claims.

According to one aspect of the invention, a method is provided for controlled operation of a biotechnological apparatus comprising one or more bioreactors, functional components each assigned to at least one bioreactor and which can be used for operational management during operation of the at least one bioreactor, and a control unit coupled to a first group of functional components in order to give control signals during operation to at least the first group of functional components are provided, wherein the method for controlling electrical power consumption for the first group of functional components during operation comprises the following steps:

provided electronic information about a predefined total electrical power consumption for the first group of functional components in the control unit, generating a respective present power control signal for the functional components of the first group of functional components in the control unit, determining, in the control unit, a currently required total electrical power consumption for a present operating situation resulting when the respective present power control signal for the first group of functional components is taken into consideration, adjusting the respective present power control signal for one or more of the functional components from the first group of functional components in order to optimise power consumption, when a comparison shows for the first group of functional components that the currently required total electrical power consumption is greater than the predefined total electrical power consumption, such that, for the first group of functional components, an adjusted total electrical power consumption is not greater than the predefined total electrical power consumption when taking into consideration the one or more adjusted power control signals and selectively remaining, unadjusted present power control signals, and outputting the one or more adjusted power control signals and the selectively remaining unadjusted present power control signals via the control unit to the functional components of the first group of functional components.

According to a further aspect of the invention, a biotechnological apparatus is provided which comprises one or more bioreactors, functional components each assigned to at least one bioreactor and which can be used for operational management during operation of the at least one bioreactor, and a control unit coupled to a first group of functional components in order to give control signals during operation to at least the first group of functional components are provided, wherein the control unit is configured to control an electrical power consumption for the first group of functional components during operation in accordance with the following steps:

providing electronic information about a predefined total electrical power consumption for the first group of functional components in the control unit, generating a respective present power control signal for the functional components of the first group of functional components in the control unit, determining, in the control unit, a currently required total electrical power consumption for a present operating situation resulting when the respective present power control signal for the first group of functional components is taken into consideration, adjusting the respective present power control signal for one or more of the functional components from the first group of functional components in order to optimise power consumption, when a comparison shows for the first group of functional components that the currently required total electrical power consumption is greater than the predefined total electrical power consumption, such that, for the first group of functional components, an adjusted total electrical power consumption is not greater than the predefined total electrical power consumption when taking into consideration the one or more adjusted power control signals and selectively remaining, unadjusted present power control signals, and outputting the one or more adjusted power control signals and the selectively remaining unadjusted present power control signals via the control unit to the functional components of the first group of functional components.

With the aid of the invention, energy-efficient operational management of the biotechnological apparatus is made possible.

One preferred development of the invention is characterised in that, when determining the currently required total electrical power consumption for the functional components from the first group of functional components, a dynamic power reserve respectively assigned to the functional components of the first group is taken into consideration. The dynamic power reserve takes dynamic variation of the individual power consumption of the functional components of the first group into account. The dynamic power reserve can be taken into account by, for example, multiplying the individual electrical power consumption by a factor greater than zero when determining the currently required total electrical power consumption for the functional components from the first group. The total consumption Pi required by the functional elements can then be calculated as follows:

$$P \cdot sum = \sum_{i=1}^{n} (1 + Pi \cdot \sigma i) \cdot |Pi \cdot SP|,$$

where P.sum is the total electrical power consumption currently required for the functional components Pi from the first group of functional components, Pi.SP is the present power control signal and Pi.σi denotes a variation, i.e. in the case where Pi.σi>0.

In one expedient variant of the invention, a step may be performed to determine the predefined total electrical power consumption for the first group of functional components, in which the predefined total electrical power consumption is determined as the difference between a maximum total electrical power consumption available for the functional components in operation and an electrical power consumption assigned to a second group of functional components, wherein the functional components of the second group, unlike the functional components of the first group, are excluded from adjustment of the present power control signal respectively assigned to them at least whenever the adjustment would cause a reduction in power for the respective functional component. The power for the functional components of the second group is preferably controlled by a power controller which is separately assigned to them. The second group is preferably formed of functional components which must fully perform their function in operation, which might be negatively affected by a reduced allocation of power. For that reason, the functional components of the second group may be exempted completely and in any case from adjustment of the present power control signal, i.e. from adjustment of the momentary setpoint values for power control. The predefined total electrical power consumption can then be determined as follows, for example: P.sum'=S.max−F.sum, where S.max is the maximum total electrical power available in operation for the functional components and F.sum is the electrical power consumption allocated to the second group of functional components.

According to one advantageous variant of the invention, a step to determine the electrical power consumption allocated to the second group of functional components is performed in such a way that a respective maximum electrical power consumption is added up for the functional components of the second group, taking into consideration a dynamic power reserve respectively allocated to the functional components. Dynamic variation in the individual power consumption of the functional components of the second group can also be taken into account by including a respective factor. The total consumption Fj of the functional elements of the second group can then be calculated as follows, for example:

$$F \cdot sum = \sum_{j=1}^{m} (1 + Fj \cdot \sigma j) \cdot |Fj \cdot PV|,$$

where F.sum is the total electrical power consumption for the functional components Fj from the second group, Fj.SP is the present power control signal and Fj.σj denotes an individually assigned variation, i.e. in the case where Fj.σj>0.

A preferred development of the invention is characterised in that a step is performed to determine the maximum total electrical power consumption available for the functional components during operation, such that a lower threshold value is determined for the maximum total available electrical power consumption, and that the lower threshold value is used when determining the predefined total electrical power consumption for the first group of functional components. In this variant, a lower threshold value is determined for the maximum total electrical power available, which is smaller than or equal to the maximum total electrical power available. The lower threshold value is then used as an initial quantity for determining the maximum total power available for the functional components of the first group, by subtracting the electrical power consumption allocated to the second group of functional components. Reference to such a lower threshold value makes it possible, for example, to provide a power buffer based on the maximum available electrical power in operation.

In one advantageous variant of the invention, the adjusted power control signal may be determined for the one or more functional components from the first group of functional components respectively in such a way that the power consumption adjusted according to the adjusted power control signal is always smaller than or equal to a maximum electrical power consumption of the respective functional component. If |Pi.SP'| denotes the amount for the power consumption determined by the adjusted power control signal, then said value is less than or equal to Pi.max. This ensures that, when adjusting the present power control signals, the adjusted power control signal adjusted for one or more functional components does not exceed the individual value for the maximum power consumption of the associated functional component. This prevents, in particular, any damage being caused to the functional components by excessive power consumption.

In one development of the invention, a relative power distribution is preserved when adjusting the respective present power control signal for a plurality of the functional components from the first group of functional components. The relative distribution of electrical power consumption resulting for the plurality of functional components from the first group due to the present power control signals is therefore preserved for the adjusted power control signals, which means that an adjustment by an equal relative value is made for all the power control signals involved.

In one embodiment of the invention, the electrical power consumption is expediently performed for functional components of one or more component types from the following group: temperature control device, sensor unit, mixing device, stirrer drive, fluid conveying device, valve and pump drive.

In another embodiment of the invention, the present power control signal for one or more of the functional components from the first group of functional components is adjusted for greater utilisation of the predefined total electrical power consumption when the comparison shows that the present total electrical power consumption is smaller for the first group of functional components than the predefined total electrical power consumption, in such a way that an adjusted total electrical power consumption results that is greater than the currently required total electrical power consumption and not greater than the predefined total electrical power consumption. In this embodiment, the result of adjustment is that, for at least one present power control signal, an adjustment is made to the effect that the currently required electrical power consumption is increased for the associated functional component. In this way, the available electrical power consumption, i.e. the predefined total electrical power consumption, is utilised to a greater extent in the present operating situation.

According to one advantageous variant of the invention, adjusting the respective present power control signal for optimising power consumption and/or adjusting the respective present power control signal for greater utilisation of the predefined total electrical power consumption includes a redistribution of power among the plurality of functional components from the first group of functional components. In this variant, adjusting the one or more present power control signals includes redistributing the electrical power consumption among at least two of the functional components in such a way that the present electrical power consumption ensuing as a result of the present power control signal is reduced for one of the functional components and increased for another of the functional components.

According to one development of the invention, one or more of the functional components from the first group of functional components are switched on and/or switched off when adjusting the respective present power control signal for optimising power consumption and/or when adjusting the respective present power control signal for greater utilisation of the predefined total electrical power consumption. In this connection, switching off or switching on may be excluded for certain operating situations or generally excluded, for one or more functional components. In this way, it is possible to ensure, for example, that individual functional components are never switched off in specially defined operating situations that are specified on the basis of one or more operating parameters of the biotechnological apparatus.

In yet another advantageous variant of the invention, the electrical power consumption for the first group of functional components may be controlled in an external control loop which is coupled to one or more internal control loops.

The object mentioned above is achieved, according to another aspect of the invention, by a biotechnological apparatus according to independent claim 14 and by a bioreactor system comprising a plurality of biotechnological apparatuses according to independent claim 20. A method according to independent claim 21 for controlling the temperature of a cultivation chamber in a biotechnological apparatus, and a method according to independent claim 24 for controlling the temperature of cultivation chambers in a bioreactor system are also provided. Advantageous embodiments of the invention are described in the dependent claims.

According to one aspect of the invention, a biotechnological apparatus is provided which comprises a bioreactor, a reactor vessel formed in the bioreactor and having a cultivation chamber, and a temperature control device provided with a heat pump and configured to control the temperature of the cultivation chamber, wherein the heat pump is thermally coupled to the cultivation chamber via the reactor vessel and to a reference body forming a heat source potential for the heat pump and made of a heat-conducting material, and transfers useful heat, with supply of drive energy, from the reactor vessel to the reference body, or vice versa.

According to another aspect of the invention, a bioreactor system is provided with comprises a plurality of biotechnological apparatuses, each comprising a bioreactor, a reactor vessel formed in the bioreactor and having a cultivation chamber, and a temperature control device configured to control the temperature of the cultivation chamber and provided with a heat pump which is thermally coupled to the cultivation chamber via the reactor vessel and to a reference body made of a heat-conducting material, and transfers useful heat, with supply of drive energy, from the respective reactor vessel to the reference body, or vice versa, wherein the reference body forms a shared heat source potential for the heat pumps of the plurality of biotechnological apparatuses.

The invention also includes the concept of a method for controlling the temperature of a cultivation chamber in a biotechnological apparatus comprising a bioreactor, a reactor vessel formed in the bioreactor and having a cultivation chamber, and a temperature control device, the method comprising the following steps:

supplying a setpoint value for a cultivation temperature in the cultivation chamber to a setpoint value input of a temperature controller, detecting a process value for the cultivation temperature using a temperature sensor unit and supplying the process value to a process value input of the temperature controller, and generating a temperature control signal by processing the setpoint value and the process value for the cultivation temperature in the temperature controller, outputting the temperature control signal via an output of the temperature controller, and receiving of the temperature control signal by a heat pump controller and controlling of the input of drive energy into the heat pump by the heat pump controller according to the temperature control signal.

A method is also provided for controlling the temperature of cultivation chambers in a bioreactor system comprising a plurality of biotechnological apparatuses, each apparatus having a bioreactor, a reactor vessel formed in the bioreactor and having a cultivation chamber, and a temperature control device, wherein the temperature in one or more of the cultivation chambers is controlled by the method specified in the foregoing.

The proposed technologies have the specific advantage over the prior art that the temperature of the cultivation chamber(s) can be controlled in an energy-efficient manner, particularly in cooling mode. Using the heat pump in the temperature control device of the respective bioreactor also has the advantage that, in comparison with the prior art, pipelines, connections and other system elements that are needed in known temperature control devices for conducting the temperature-control fluid can be done without. This also means that no leakages of temperature-control fluid can occur, which might in certain circumstances cause damage to components of the bioreactor, or result in operational failure. In operation, the heat pump can be controlled exactly in order to adjust the desired heat exchange between the bioreactor and the reference body according to present operational management requirements.

The proposed technologies, which specifically stipulate the use of one or more heat pumps, also support more extensive integration of the biotechnological apparatuses and a compact structure, particularly in parallel bioreactor systems.

The at least one bioreactor may be, in particular, an autoclavable bioreactor or a single-use bioreactor. The latter is preferably provided in sterile packaging. However, the proposed technologies can also be used in their various embodiments in hybrid variants of bioreactors.

In one preferred development of the invention, the heat pump is a heat pump which can be driven by electrical drive energy. In one variant, the heat pump is designed with at least one Peltier element.

In one expedient configuration of the invention, the reactor vessel may be disposed in a vessel receptacle, and the heat pump may be in thermally coupled to the reactor vessel via the vessel receptacle. The vessel receptacle acts as a heat exchanger and preferably consists of a material which conducts heat well. The reactor vessel and/or the vessel receptacle form a thermal demarcation of the cultivation chamber from the operating environment of the bioreactor. In addition, the vessel receptacle may also be provided with thermal insulation on the outside.

In one advantageous embodiment of the invention, the reference body is thermally coupled to an operating environment of the bioreactor. The heat source potential of the reference body is then in relation to the ambient temperature, for example. The operating environment of the bioreactor itself, in particular the ambient air, may be subject to temperature control, in particular by using air conditioning, for example to reduce the influence of, or to compensate entirely for varying temperatures during the day and/or for seasonal effects. In that respect, one or more heat exchangers or air conditioning compressors may also be part of the operating environment. Such elements, which then are likewise part of the operating environment, may also be coupled directly to the reference body in order to influence its heat potential, in addition to or superpositioned with the influence of ambient air.

In one development of the invention, the reference body is preferably thermally coupled to the operating environment of the bioreactor via an adjustable thermal resistance. The heat potential of the reference body can be controlled accordingly by activating the adjustable thermal resistance of the operational management of the bioreactor. The flow of heat between the reference body and the operating environment can be viewed as the quotient of the difference between the ambient temperature and the temperature of the reference body, and the thermal resistance. By varying the thermal resistance, it is possible to adjust the flow of heat between the reference body and the operating environment. Variable transfer of heat can be carried out in this context by using a heat sink, for example, and a variable fan control assigned to the latter.

In one advantageous variant of the invention, the heat pump may be coupled to a controller which is configured to control, during operation of the bioreactor, the supply of drive energy for transferring the useful heat from the reactor vessel to the reference body, or vice versa, in accordance with a predefined operational management scheme. The controller may be designed with one or more control or regulation components that perform a comparison of setpoint and process values, in particular, in order to derive regulation or control signals. In a simple case, the temperature in the cultivation chamber may be detected and compared with a setpoint temperature in order to derive a control signal which then controls the heat pump assigned to the bioreactor.

In combination with the method for controlling the temperature of a cultivation chamber in a biotechnological apparatus, external temperature control may be performed by means of the temperature controller and internal temperature control may be performed by means of an additional temperature controller, the method then further comprising the following steps:

supplying the temperature control signal outputted by the temperature controller to a setpoint value input of the additional temperature controller, detecting a process value for the temperature of a heat exchanger via which the heat pump is thermally coupled to the reactor vessel, by means of an additional temperature sensor unit and supplying the process value to a process value input of the additional temperature controller, generating an adjusted temperature control signal by processing the setpoint value and the process value in the additional temperature controller, outputting the adjusted temperature control signal via an output of the additional temperature controller, and receiving of the adjusted temperature control signal by the heat pump controller and controlling of the input of drive energy into the heat pump by the heat pump controller according to the adjusted temperature control signal.

The temperature controller and/or the additional temperature controller may be designed as a PID (Proportional Integral Derivative) controller, for example, including use of a software implementation, in particular. The heat pump can be protected against overload by limiting the setpoint values at one or more regulators.

Another variant of the method comprises the following steps:

supplying a power control signal corresponding to the temperature control signal/the adjusted temperature control signal to a setpoint value input of a power controller included in the heat pump controller, detecting a process value for electrical power consumed by the heat pump and supplying the process value to a process value input of the power controller, generating an adjusted power control signal by processing the setpoint value and the process value in the power controller, outputting the adjusted power control signal via an output of the power controller, and receiving of the adjusted power control signal by a controller of the heat pump controller assigned to the heat pump and controlling of the input of drive energy into the heat pump by means of the controller in accordance with the adjusted power control signal.

In this variant, the controller coupling to the heat pump includes, in addition to a respective control loop for the internal temperature control and/or the external temperature control, an additional control loop with which a control signal influencing the electrical power consumption is generated, which is then used here to adjust the heat pump, ultimately. The power controller used to generate the power control signal controls the actuating member of the heat pump such that the process value of the electrical power induced into the heat pump is equal to the setpoint value. A control mechanism optimising the power for the temperature control devices has thus been provided.

The process value of an induced power is determined in the case of electrical heat pumps by measuring current consumption and voltage supply, for example. The efficiency of the actuating member, in the form of PWM full bridges (H-bridges), for example, can be taken into account in this connection. This is done, more specifically, in a closed loop variant. The power controller, which can be a PID controller, may be configured to compensate for nonlinearities or serial spreads in the assigned heat pump. When using the plurality of control loops, the adjustment speed of the power controller ranges from a few milliseconds to a maximum of about one second. The control dynamics of the internal temperature control loop for generating the adjusted temperature control signal typically ranges between several seconds to a few minutes. The adjustment speed of the external temperature controller ranges, for example, from one-digit to two-digit minute values.

In connection with the method for controlling the temperature of cultivation chambers in a bioreactor system comprising a plurality of biotechnological apparatuses, the heat pump of the temperature control device of one of the plurality of biotechnological apparatuses may, in one operating phase of the bioreactor system, transfer useful heat from the reactor vessel to the reference body in order to cool the cultivation chamber, and the heat pump of the temperature control device of another of the plurality of biotechnological apparatuses may be assigned to transfer useful heat from the reference body to the reactor vessel in order to heat it. Thus, during cooling in a bioreactor, useful heat is supplied simultaneously in another bioreactor in order to heat the cultivation chamber. Since the reference body is used as a shared heat potential for the several heat pumps of the bioreactor, heat is simultaneously supplied to it and removed from it. In this way, the temperature control process can be carried out in an particularly energy-efficient manner for the apparatus comprising a plurality of bioreactors. Individual control of the temperature control devices, which are each assigned to a particular bioreactor, thus allows efficient power management for the arrangement of bioreactors in the bioreactor system.

The following embodiments may be additionally provided in combination with the various aspects of the biotechnological apparatus as described above, or alternatively thereto.

A method for controlled operation of a biotechnological apparatus comprising one or more bioreactors, functional components each assigned to at least one bioreactor and which can be used for operational management during operation of the at least one bioreactor, and a control unit coupled to a first group of functional components in order to give control signals during operation to at least the first group of functional components are provided, wherein the method for controlling electrical power consumption for the first group of functional components during operation comprises the following steps:

providing electronic information about a predefined total electrical power consumption for the first group of functional components in the control unit, generating a respective present power control signal for the functional components of the first group of functional components in the control unit, determining, in the control unit, a currently required total electrical power consumption for a present operating situation resulting when the respective present power control signal for the first group of functional components is taken into consideration, adjusting the respective present power control signal for one or more of the functional components from the first group of functional components in order to optimise power consumption, when a comparison shows for the first group of functional components that the currently required total electrical power consumption is greater than the predefined total electrical power consumption, such that, for the first group of functional components, an adjusted total electrical power consumption is not greater than the predefined total electrical power consumption when taking into consideration the one or more adjusted power control signals and selectively remaining, unadjusted present power control signals, and outputting the one or more adjusted power control signals and the selectively remaining unadjusted present power control signals via the control unit to the functional components of the first group of functional components.

A biotechnological apparatus comprising one or more bioreactors, functional components each assigned to at least one bioreactor and which can be used for operational management during operation of the at least one bioreactor, and a control unit coupled to a first group of functional components in order to give control signals during operation to at least the first group of functional components are provided, wherein the control unit is configured to control an electrical power consumption for the first group of functional components during operation in accordance with the following steps:

providing electronic information about a predefined total electrical power consumption for the first group of functional components in the control unit, generating a respective present power control signal for the functional components of the first group of functional components in the control unit, determining, in the control unit, a currently required total electrical power consumption for a present operating situation resulting when the respective present power control signal for the first group of functional components is taken into consideration, adjusting the respective present power control signal for one or more of the functional components from the first group of functional components in order to optimise power consumption, when a comparison shows for the first group of functional components that the currently required total electrical power consumption is greater than the predefined total electrical power consumption, such that, for the first group of functional components, an adjusted total electrical power consumption is not greater than the predefined total electrical power consumption when taking into consideration the one or more adjusted power control signals and selectively remaining, unadjusted present power control signals, and outputting the one or more adjusted power control signals and the selectively remaining unadjusted present power control signals via the control unit to the functional components of the first group of functional components.

With the aid of the above technologies, energy-efficient operational management of the biotechnological apparatus is made possible.

One preferred development is characterised in that, when determining the currently required total electrical power consumption for the functional components from the first group of functional components, a dynamic power reserve respectively assigned to the functional components of the first group is taken into consideration. The dynamic power reserve takes dynamic variation of the individual power consumption of the functional components of the first group into account. The dynamic power reserve can be taken into account by, for example, multiplying the individual electrical power consumption by a factor greater than zero when determining the currently required total electrical power consumption for the functional components from the first group. The total consumption Pi required by the functional elements can then be calculated as follows:

$$P.sum = \sum_{i=1}^{n} (1 + Pi \cdot \sigma i) \cdot |Pi \cdot SP|,$$

where P.sum is the total electrical power consumption currently required for the functional components Pi from the first group of functional components, Pi.SP is the present power control signal and Pi.σi denotes a variation, i.e. in the case where Pi.σi>0.

In one expedient variant, a step may be performed to determine the predefined total electrical power consumption for the first group of functional components, in which the predefined total electrical power consumption is determined as the difference between a maximum total electrical power consumption available for the functional components in operation and an electrical power consumption assigned to a second group of functional components, wherein the functional components of the second group, unlike the functional components of the first group, are excluded from adjustment of the present power control signal respectively assigned to them at least whenever the adjustment would cause a reduction in power for the respective functional component. The power for the functional components of the second group is preferably controlled by a power controller which is separately assigned to them. The second group is preferably formed of functional components which must fully perform their function in operation, which might be negatively affected by a reduced allocation of power. For that reason, the functional components of the second group may be exempted completely and in any case from adjustment of the present power control signal, i.e. from adjustment of the momentary setpoint values for power control. The predefined total electrical power consumption can then be determined as follows, for example: P.sum'=S.max−F.sum, where S.max is the maximum total electrical power available in operation for the functional components and F.sum is the electrical power consumption allocated to the second group of functional components.

According to one advantageous variant, a step to determine the electrical power consumption allocated to the second group of functional components is performed in such a way that a respective maximum electrical power consumption is added up for the functional components of the second group, taking into consideration a dynamic power reserve respectively allocated to the functional components. Dynamic variation in the individual power consumption of the functional components of the second group can also be taken into account by including a respective factor. The total consumption Fj of the functional elements of the second group can then be calculated as follows, for example:

$$F.sum = \sum_{j=1}^{m} (1 + Fj \cdot \sigma j) \cdot |Fj \cdot PV|,$$

where F.sum is the total electrical power consumption for the functional components Fj from the second group, Fj.SP is the present power control signal and Fj.σj denotes an individually assigned variation, i.e. in the case where Fj.σj>0.

A preferred development is characterised in that a step is performed to determine the maximum total electrical power consumption available for the functional components during operation, such that a lower threshold value is determined for the maximum total available electrical power consumption, and that the lower threshold value is used when determining the predefined total electrical power consumption for the first group of functional components. In this variant, a lower threshold value is determined for the maximum total electrical power available, which is smaller than or equal to the maximum total electrical power available. The lower threshold value is then used as an initial quantity for determining the maximum total power available for the functional components of the first group, by subtracting the electrical power consumption allocated to the second group of functional components. Reference to such a lower threshold value makes it possible, for example, to provide a power buffer based on the maximum available electrical power in operation.

In one advantageous variant, the adjusted power control signal may be determined for the one or more functional components from the first group of functional components respectively in such a way that the power consumption adjusted according to the adjusted power control signal is always smaller than or equal to a maximum electrical power consumption of the respective functional component. If |Pi.SP'| denotes the amount for the power consumption determined by the adjusted power control signal, then said value is less than or equal to Pi.max. This ensures that, when adjusting the present power control signals, the adjusted power control signal adjusted for one or more functional components does not exceed the individual value for the maximum power consumption of the associated functional component. This prevents, in particular, any damage being caused to the functional components by excessive power consumption.

In one development, a relative power distribution is maintained when adjusting the respective present power control signal for a plurality of the functional components from the first group of functional components. The relative distribution of electrical power consumption resulting for the plurality of functional components from the first group due to the present power control signals is therefore maintained for the adjusted power control signals, which means that an adjustment by an equal relative value is made for all the power control signals involved.

In combination with advantageous developments of the biotechnological apparatus, the observations made in the foregoing with regard to expedient variants of the method apply accordingly.

DESCRIPTION OF PREFERRED EMBODIMENTS OF THE INVENTION

Figure 2:
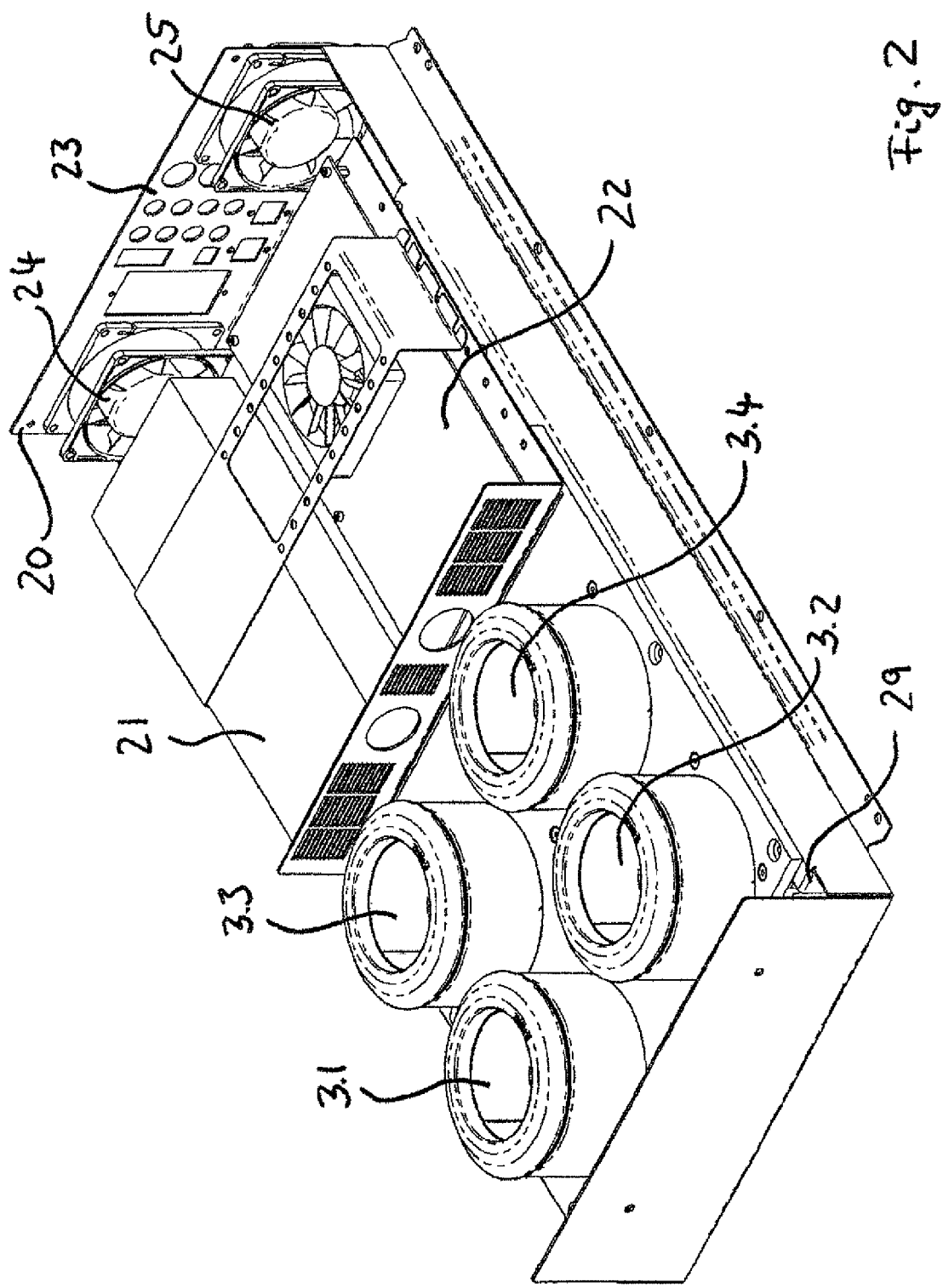
Figure 3:
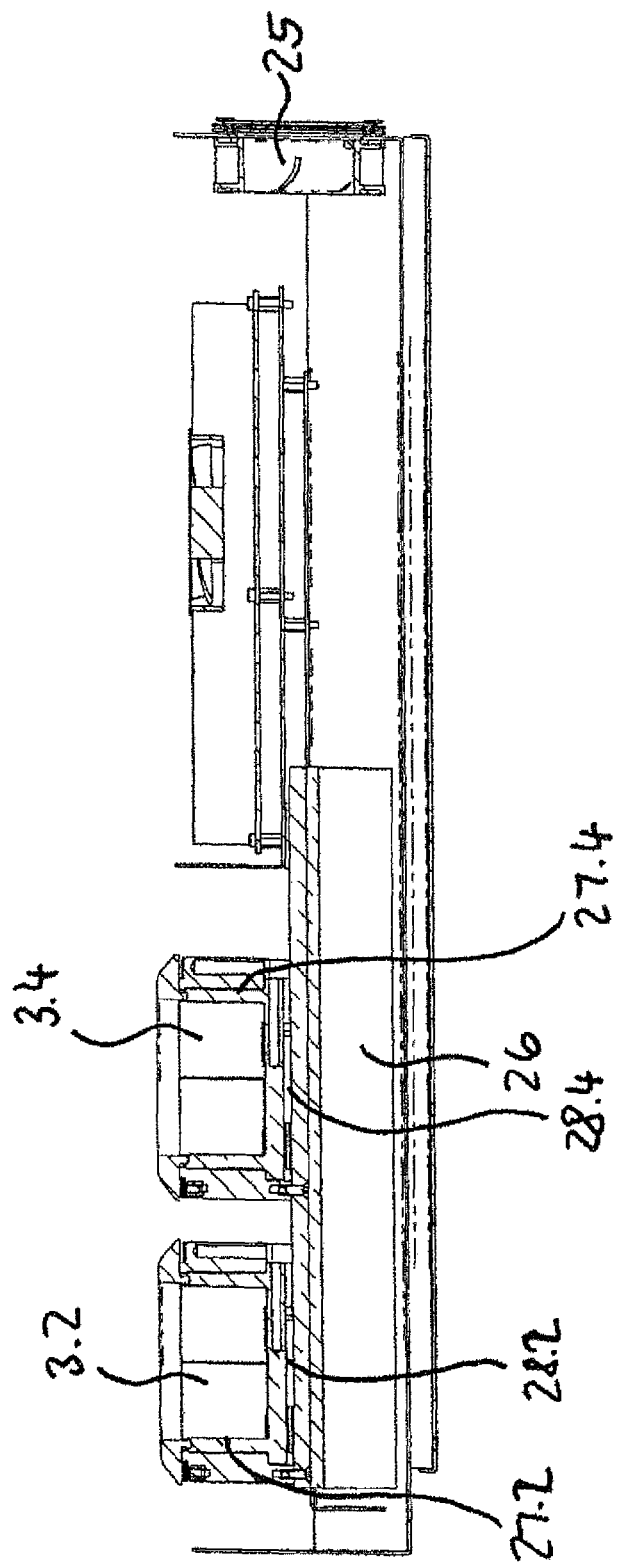
Figure 4:
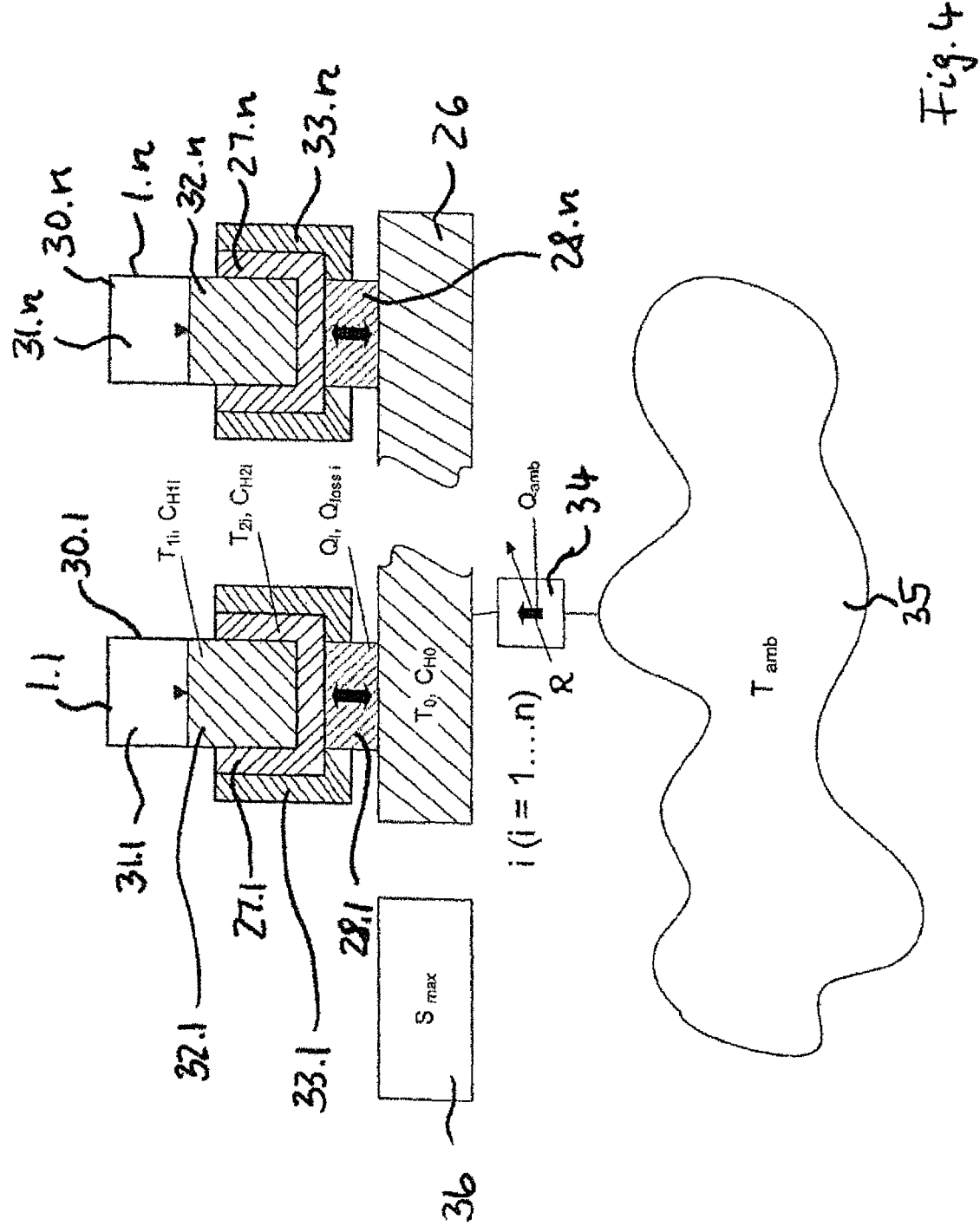
Figure 5:
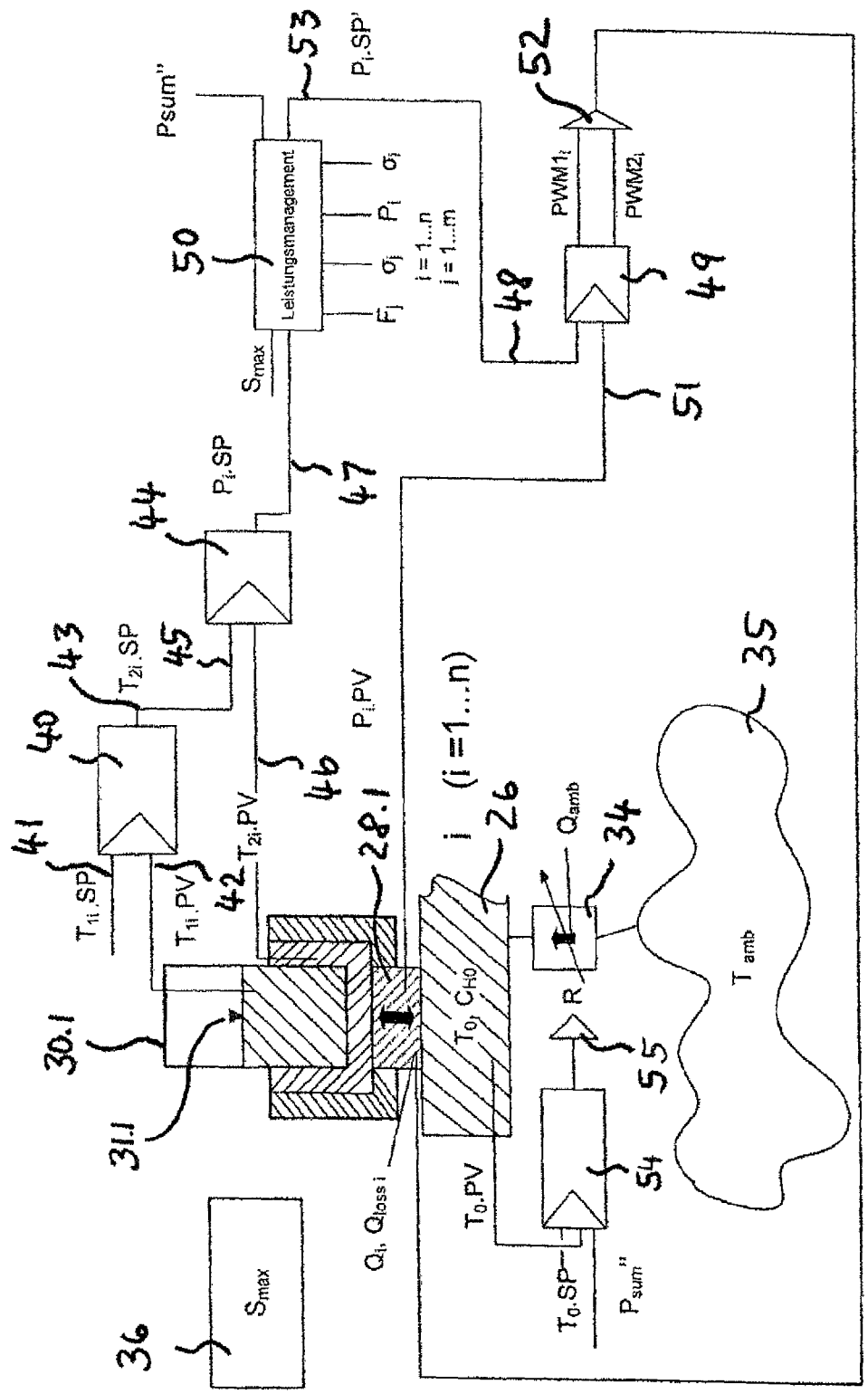
Figure 6:
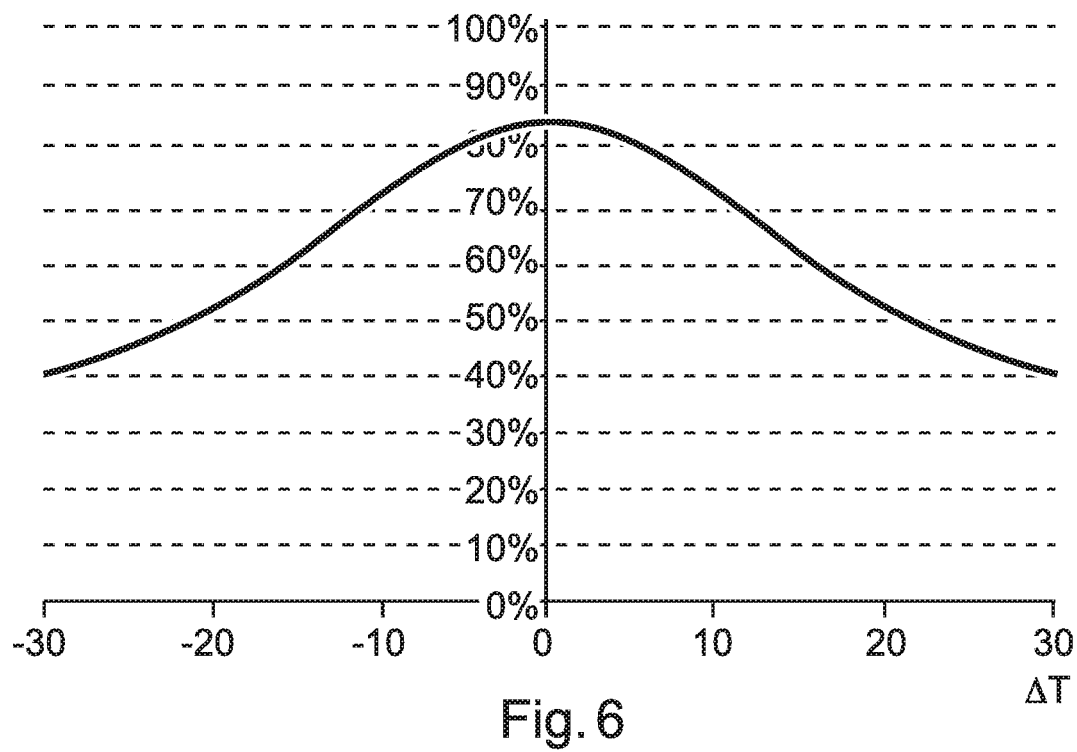
Figure 7:
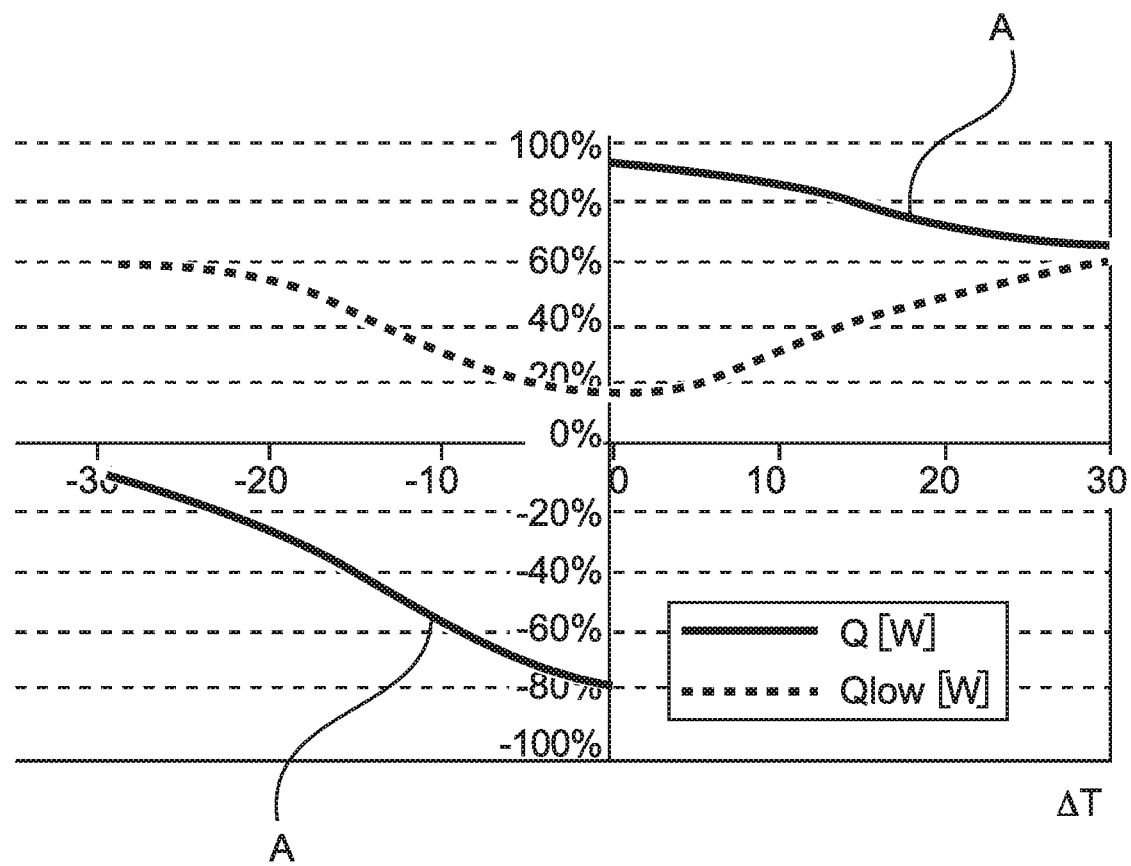

The invention shall now be described with reference to preferred embodiments and to the Figures, in which FIG. 1 shows a view of a biotechnological apparatus comprising a bioreactor system formed by a plurality of bioreactors, FIG. 2 shows a view of a temperature controller of the bioreactor system in FIG. 1, FIG. 3 shows a sectional view of the temperature controller in FIG. 2, FIG. 4 shows a schematic view of a biotechnological apparatus comprising a bioreactor system formed by a plurality of bioreactors which are each thermally coupled, via a heat pump, to a shared source or main thermal potential, FIG. 5 shows another schematic view of the biotechnological apparatus in FIG. 4, with a control unit assigned thereto, FIG. 6 is a graph showing the dependency of the efficiency (in percent) of an electrically controllable heat pump in dependency on the temperature differential ΔT between thermally coupling faces and FIG. 7 is a graph showing how the efficiency (in percent) of a heat pump depends on the temperature differential ΔT.

FIG. 1 shows a schematic view of a biotechnological apparatus comprising a bioreactor system embodied with a plurality of bioreactors $1.1, \ldots, 1.4$, which are releasably received for operation in respectively assigned openings $3.1 \ldots 3.4$ in a base block 2, such that each of the plurality of bioreactors $1.1 \ldots 1.4$ is coupled to a temperature controller which is disposed in base block 2. Bioreactors $1.1 \ldots 1.4$ are each fitted with connection members $4.1 \ldots 4.4$ for supplying or removing fluids necessary for operation.

An arrangement 5 with containers is formed on base block 2.

According to FIG. 1, two more functional blocks 6, 7 are also arranged in a stack on basic functional block 2, which can be removed and which can receive a gas mixing station, for example, and/or one or more pumps.

In the base block 2 of the bioreactor system in FIG. 1, a temperature controller for bioreactors $1.1, \ldots, 1.4$ is implemented, and which is used to adjust, during operation of bioreactors $1.1 \ldots 1.4$, the operating conditions in respect of temperature desired for cultivation. The temperature controller shall now be described in more detail with reference to FIGS. 2 and 3, which show a schematic view of a temperature control device of the bioreactor system in FIG. 1 and a cross-section of the temperature control device shown in FIG. 2.

According to FIG. 2, a power unit 21 and control electronics 22 are arranged adjacent to each other in a housing 20. On one housing rear side 23, fans 24, 25 are integrated into the wall of housing 20, which are assigned to and cooperate with a reference body 26 (cf. FIG. 3) acting as a heat source potential, in such a way that fans 24, 25 generate an flow of air for reference body 26 that has the temperature of the operating environment of the bioreactor system, in order in this way to ensure heat exchange between the ambient air and reference body 26.

According to FIG. 3, openings 3.2, 3.4 for bioreactors 1.2, 1.4 are formed in respective vessel receptacles 27.2, 27.4, each of which is thermally coupled to a heat pump 28.2, 28.4 disposed thereunder, which for its part is then thermally coupled to the reference body 26 which is located thereunder and which forms the main thermal potential. In the embodiment shown here, heat pumps 28.2, 28.4 are each formed by at least one Peltier element, that is, they are embodied as heat pumps which can be driven by electrical energy. By supplying electrical drive energy, heat pumps 28.2, 28.4 are driven during operation of the bioreactor system in order to induce a transfer of heat from the respective vessel receptacle 27.2, 27.4 to reference body 26, or vice versa. In this way, the temperature of the respective vessel receptacle 27.2, 27.4, which thus acts as a heat exchanger, and ultimately that of the associated bioreactor 1.2, 1.4 is controlled in operation, be it to cool it or to heat it.

As can be seen from FIG. 2, reference body 26 has cooling fins 29 which are formed along its overall length. Between cooling fins 29, the air flow produced by fans 24, 25 flows.

The structure and function of the temperature controller or regulator for the bioreactors shall now be described in the following with reference to FIGS. 4 to 7. In FIGS. 4 and 5, the same reference signs for the same features as in FIGS. 1 to 3 are used.

FIG. 4 shows a schematic view of a biotechnological apparatus comprising a bioreactor system formed by a plurality of bioreactors $1.1, \ldots, 1.n$ which are each thermally coupled, via an associated heat pump $28.1, \ldots, 28.n$, to a shared source or main thermal potential formed by reference body 26.

Reference body 26 consists of a material with high thermal conductivity. The present temperature of reference body 26 is designated T0, and its specific heat capacity CH0. The plurality of bioreactors $1.1, \ldots, 1.n$ are unilaterally thermally coupled to the reference body 26 forming the main thermal potential. Bioreactors $1.1, \ldots, 1.n$ each comprise a reactor vessel $30.1, \ldots, 30.n$ which is arranged in the associated vessel receptacle $27.1, \ldots, 27.n$, and the cultivation chamber $31.1, \ldots, 31.n$ of which is partially filled with a culture $32.1, \ldots, 32.n$ being cultivated. Vessel receptacle $27.1, \ldots, 27.n$ is thermally insulated on the outside against the surroundings by means of insulation means $33.1, \ldots, 33.n$.

In the respectively assigned heat pump $28.1, \ldots, 28.n$, which is preferably designed as an electrically driven heat pump, for example by means of at least one Peltier element, a positive or negative flow of heat Qi is induced from reference body 26 to vessel receptacle $27.1, \ldots, 27.n$, or vice versa, depending on how the heat pump is controlled. Two heat loss flows Qlossi/2, which are always positive, are added to this flow of heat.

According to FIG. 4, reference body 26 is thermally coupled to the operating environment 35 via a thermal resistance 34. Operating environment 35 has the current, predefined temperature Tamb. A flow of heat between reference body 26, which forms the main thermal potential, and operating environment 35 equates to $Q_{Amb}=(T_{amb}-T_0)/R$.

By suitable variation of the thermal resistance 34, $Q_{Amb}$ and $T_0$ can be suitably controlled within desired ranges during operation of the bioreactor. In practice, the variably adjustable heat transfer can be carried out with the aid of the combination of a heat sink and a controllable fan device (in this regard, see also the description above in respect of FIGS. 2 and 3).

According to FIG. 4, an electrical power supply 36 is also provided for heat pumps $28.1, \ldots, 28.n$, for which a maximum power level S.max is predefined.

The efficiency of electrically controllable heat pumps is significantly affected by the temperature differential between the two coupling faces. This relationship is represented qualitatively in the following FIGS. 6 and 7. FIG. 6 is a graph showing the dependency of the efficiency (in percent) of an electrically controllable heat pump in dependency on the temperature differential ΔT between thermally coupling faces.

The maximum efficiency is achieved when ΔT=0K, and the efficiency decreases with increasing temperature differential. The inputted power is split into an effective heat flow Qi and a heat loss flow Qlossi. Whereas the heat loss flows make a positive contribution, from the perspective of the process target, when heating the culture they deteriorate the situation in the case of cooling. These relationships are illustrated in FIG. 7 for a given power inputted to the heat pump (curve A-Qeff). FIG. 7 is a graph showing how the efficiency (in percent) of a heat pump depends on the temperature differential ΔT. Whereas in the case of heating (to the right of the y-axis) a large proportion of the inputted power directly benefits the biological culture, the efficiency decreases strongly with increasing temperature differential in the case of cooling (to the left of the y-axis). To achieve an optimal design of the system as a whole (maximum efficiency), the setpoint temperature T0.SP (SP="Set Point"=setpoint value) of the main potential should therefore be made less than or equal to the setpoint temperature T1$i$.SP of the cultures in the bioreactors.

Control mechanisms for controlling the temperature in bioreactors 1.1, . . . , 1.$n$ shall now be described in more detail with reference to FIG. 5.

Heat pumps 28.1, . . . , 28.$n$ are each thermally coupled to reference body 26, which forms the main thermal potential. In a typical operational management system, a plurality of bioreactors 1.1, . . . , 1.$n$ are heated, which corresponds to a positive flow of heat from reference body 26 to the respective bioreactor. This results in reference body 26 cooling down. If one or more other bioreactors are cooled at the same moment of operation, this leads to positive heat exchange flows from the heat pumps assigned to these bioreactors to reference body 26. If operational management is ideal, the exchanges of heat to and from reference body 26 complement each other in such a way that no change in the temperature of reference body 26 occurs, or only a very slight change of temperature. The system as a whole then operates with maximum energy efficiency.

For by far the greatest proportion of biological metabolisms, the optimal and hence also the typical temperature range for such applications is between about 25 and 40° C. The metabolic processes are accompanied by the biological systems generating (specific) heat, the maximum of which is therefore likewise within the aforementioned temperature range. The bioreactor systems preferably considered her are typically operated in laboratory rooms having an ambient temperature Tamb of approximately 20 to approximately 30° C. When appropriately dimensioned, T0 of the reference body 26 may therefore be operated close to Tamb. In this situation, with T1$i$, T2$i$ within the biologically relevant operating range of approximately 25 to approximately 40° C., and T0 close to Tamb at approximately 20 to approximately 30° C., the temperature differential between the coupling faces of heat pumps 28.1, . . . , 28.$n$ is small, as a result of which their efficiency is high.

If the dynamics of the metabolic process in one or several of the cultures are now to be changed at a given moment, which corresponds to the cooling function that is frequently used in practice, the system starts close to the working point that is ideal in this respect. Although the efficiency of the heat pumps in question decreases in the course of cooling, due to the increasing temperature differential between the coupling faces, the biological activity also decreases simultaneously, as does the specific generation of heat by the cultures, with the result that the effects partially compensate for each other.

According to FIG. 5, the setpoint value (SP) for the culture temperature T1$i$.SP (i=1, . . . , n) is predefined to an external temperature controller 40, which may be a modified PID controller, for example, that is implemented at least partially by means of the operating software. The setpoint value (SP) for the culture temperature T1$i$.SP is given to a setpoint value input 41 of the external temperature controller 40. A process value T1$i$.PV (PV—"Process Value") is given to a process value input 42 of the external temperature controller 40. The controller output signal is calculated by comparing the setpoint temperature and the process temperature T1$i$.PV and by taking into account the controller parameter, and it is outputted via an output terminal 43 of the external temperature controller 40. This signal is simultaneously the setpoint temperature for vessel receptacle 27.1 with the designation T2$i$.SP, which is given to an internal temperature controller 44 at a setpoint value input 45. The process value T2$i$.PV is applied to the process value input 46 of the internal temperature controller 44.

The maximum temperature differential between the temperature in the cultivation chamber 31.1 and the temperature in the reactor vessel 30.1 or in vessel receptacle 27.1 can be defined by suitable upper and lower limits for the value T2$i$.SP, either in absolute terms or relative to the culture temperature T1$i$.SP or T1$i$.PV. Damage to the biological systems due to overheating or overcooling can be prevented effectively in this way.

The internal temperature controller 44, which may also be a modified PID controller implemented by means of software, for example, calculates a controller output signal Pi.SP from the setpoint value T2$i$.SP and the process value of the vessel receptacle 27.1 T2$i$.PV, taking the controller parameters into account. The controller output signal Pi.SP is outputted via an output terminal 47 and is applied to a control block 50. By suitably limiting this setpoint value Pi.SP, heat pump 28.1 can be protected against overload. It is also possible in this way to implement load distribution throughout the system, as will be described in more detail below. Control block 50 is used in this regard to implement the higher-level power management. An adjusted control signal Pi.SP' is outputted via an output terminal 53 and is supplied to a setpoint value input 48 of power controller 49 (see below for further description).

The process value Pi.PV is supplied to the process value input 51 on power controller 49. Power controller 49 controls a controller 52 of heat pump 28.1 such that the process value of the power Pi.PV induced into heat pump 28.1 corresponds to the setpoint value Pi.SP' which is outputted by control block 50. The process value Pi.PV of the induced power is typically determined in the case of electrical heat pumps by measuring current consumption and voltage supply. The efficiency of controller 52, which is realised by PWM full bridges, for example, and which is also referred to as "power electronics of the associated heat pump", may be arithmetically taken into account, as indicated by way of example in the following table:

| | |
|---|---|
| Supply voltage of the power electronics | U |
| Measured current consumption of the power electronics of heat pump i | $I_i$ |
| Power transferred from the power supply to the power electronics of heat pump i, which is taken into account in the power balance for the system as a whole. | $P_{Total\ i} = U \cdot I_i$ |
| Shunt resistance of current measurement | $R_S$ |
| Power loss from current measurement i | $P_{Loss\ i} = R_S \cdot I_i^2$ |
| Efficiency of the power electronics i (PWM full bridge) | $\eta_i$ |
| Process value of the power transferred at heat pump i (Process Value = PV), which is used for optimised power control of heat pump i. | $P_i.PV = \eta_i \cdot (P_{Total\ i} - P_{Loss\ i})$ $P_i.PV = \eta_i \cdot (U \cdot I_i - R_S \cdot I_i^2)$ |

In the embodiment described by way of example, power controller 49 compensates for the nonlinearities and serial spreads that frequently occur in practice in respect of heat pump 28.1. Power controller 49 actively linearises the behaviour of heat pump 28.1 that is in use. Component variances are also compensated by the direct measurement of power. A robust controller is thus formed which also works efficiently, since it is not necessary during production to sort elements.

In a simplified embodiment, the output signal of the external temperature controller 40 can be used directly to control controller 52, by leaving out the internal temperature controller 44 and the power controller 49. In an alternative embodiment, the internal temperature controller 44 can be connected downstream from the external temperature controller 40, without power controller 49 being used. In another embodiment, output 43 can be given directly to the setpoint value input 48 of power controller 49.

The dynamics of the control loop increase with the external temperature controller 40, the internal temperature controller 44 and the power controller 49 analogously with the (continuously decreasing) heat capacities of the respective system components to be subjected to temperature control. Typical adjustment speeds of power controller 49 range from a few milliseconds to a maximum of one second. The control dynamics of the internal temperature controller 44 typically range from several seconds to a few minutes. The adjustment speed of the external temperature controller 40 can normally span a range from single-digit to two-digit minute values.

The interconnected control loops each linearise the transfer characteristics of the controlled systems assigned to them. This results in very exact and narrowly defined control with considerable robustness.

Each of the interconnected control loops is optimally adjusted in respect of its control parameters to the dynamic transfer characteristics of the controlled system assigned to it. To achieve this, the dynamic behaviour of the control loops can be determined experimentally in advance, and information about the determined dynamics, for example the operating parameters characterising the dynamic behaviour, can be stored in software. Such an approach is well-known as such and does not require any further explanation here. In this way, optimal control dynamics for the system as a whole are achieved.

A further controller 54 controls the thermal resistance 34 of the coupling between the reference body 26 forming the main potential and the surrounding 35, according to the setpoint and process value of temperature TO and the present load situation. It uses an actuating member 55 for that purpose, which may take the form of fans 24, 25, for example.

By specifically defining and controlling the maximum temperature differentials between the temperature in cultivation chamber 31.1, . . . , 31.n and the temperature of reactor vessel 30.1, . . . , 30.n of vessel receptacle 27.1, . . . , 27.n, possible damage caused to the biological systems in the culture by overheating or over-cooling are actively prevented. This can also be ensured for transients/transfers, due to the strong system dynamics of the internal temperature control loops comprising controllers 44, 49.

For reasons of cost efficiency and also for electrical safety reasons, the device for managing the bioreactor temperatures may be operated with multi-voltage power supply units, so called, which convert the country-specific primary voltage into a uniform safe extra-low voltage.

Control block 50 (cf. FIG. 5), in particular, sums the power consumptions of all n-setpoint values Pi.SP. This summed signal P.sum is used for load distribution throughout the system, in particular for managing distribution of the electrical power individually allocated to heat pumps 28.1, . . . , 28.n. Other functional components of the biotechnological apparatus can also be included in such a (higher-level) power management system, or the latter may be provided only for functional components in which heat pumps 28.1, . . . , 28.n are not even included. It is therefore assumed in the following that the group in question is any arbitrary group of functional elements of the biotechnological apparatus, which in a special case may then be heat pumps 28.1, . . . , 28.n.

The functional components Pi have the following characteristics:

| | |
|---|---|
| Pi · max | Maximum power consumption of functional component Pi |
| Pi · SP | Power setpoint value predefined by higher-level operational management system. The value of Pi · SP is always less than |
| \|Pi · SP\| <= Pi · max | or equal to Pi · max, thus preventing in an effective manner any overloading of the actuating member, in particular. By modifying Pi · SP on a time-dependent basis, for example by means of an integrating control portion, the high-level load management system can affect the prioritisation of the functional components in the power management allocation procedure (see below for more detail). |
| Pi · SP' | Power setpoint value allocated by the power management system according to a specific distribution strategy. The value |
| \|Pi · SP'\| <= \|Pi · SP\| | of Pi · SP' is not greater than the value of Pi · SP. In the embodimen tabove, the latter value is supplied as a valid setpoint value to power controller 49. (For switching actuating members, Pi · SP' is either equal to Pi · SP or zero.) |
| Pi · PV | Process value for the power consumption of the functional component Pi. (Is set, for example, by means of power controller 49, usually in highly dynamic manner, according to the set according to the predefined setpoint value Pi · SP'.) |
| Pi · σ | Typical percentual dynamic variation in power Pi · PV. May be relatively small if controller is well designed, for example within a range of 1 to 3%. |

The biotechnological apparatus may also comprise other functional components Fj (j=1, . . . , m) which are not subjected directly to power management, but which instead supply external, time-based conditions for power management. Typical embodiments for the other functional components Fj are stirrer drives, gas mixing systems, valves and/or pump drives.

In contrast to functional components Pi, for which a slight delay in adjustment caused by reduced power allocation can easily be coped with, certain functional components must be able to perform their function in full at all times. For that reason, such components should not be disrupted by reduced power allocation, which can otherwise occur under the proposed power management system.

The other functional components Fj have the following characteristics:

| | |
|---|---|
| Fj.max | Maximum power consumption of the other functional components Fj, which is safeguarded with the aid of a power controller assigned directly to the respective other functional component. |
| Fj.PV | Process value for the power consumption of the other functional component Fj |
| \|Fj.PV\| <= Fj.max | |
| Fj.σ | Percentual dynamic variation in power Fj.PV |

A power supply S is provided for functional components Pi and for the other functional components Fj, namely by electrical power supply 36 in the embodiment described above.

The power supply S has the following characteristics.

| | |
|---|---|
| S.max | Maximum output power of power supply S.<br>(The maximum power output may vary within a certain range over time, depending on external factors such as time of day, temperature of the operating environment or energy prices, but may not fall under a predefined minimum value.) |
| S.PV <= S.max | Present power output of energy supply S. |

In order to specify the minimum output power S.max, the electrical power consumptions for functional components Pi and for the functional components Fj can be based, if known, on simultaneity factors. The following variant is based on a simultaneity of the other functional components Fj of 1, i.e. all the components can be operated simultaneously with Fj.max.

The first step is to determine the sum of the maximum power consumptions of the functional components Pi:

$$P \cdot \max = \sum_{i=1}^{n} Pi \cdot \max$$

The sum of the maximum power consumptions of the other functional components Fj is then calculated:

$$F \cdot \max = \sum_{j=1}^{n} Fj \cdot \max$$

The minimum value of the maximum power output of power supply S is dimensioned:

$$S \cdot \max = \alpha \cdot \sum_{i=1}^{n} Pi \cdot \max + \sum_{j=1}^{m} Fj \cdot \max$$

Factor $\alpha$ is theoretically within the range [0 . . . 1] and is usually selected, depending on application, in the range [0.2 . . . 0.8], for example.

In the biotechnological apparatus described above, with heat pumps $28.1, \ldots, 28.n$ (cf. FIG. 5), the biggest proportion of the installed power rating is usually found in the functional elements Pi for temperature control.

The complete installed power of heat pumps $28.1, \ldots, 28.n$ is required in rare cases only; furthermore, there is only a slight probability in such cases that the maximum power Fj.max will be required by the other functional components Fj. This means that the factor a can be selected with a relatively low value [0.2, . . . , 0.5]. This avoids any over-dimensioning of the power supply, with the concomitant negative consequences such as costs, power loss, cut-in currents, etc.

In the following, a method for determining the distribution of electrical power consumption shall be described with an example. In the first step, the present operating situation with regard to electrical power consumption is determined.

The total required power consumption of the functional elements Pi is determined. As an option, an individual dynamic reserve may be taken into account here using a variation Pi.σi, i.e. in the case where Pi.σi>0:

$$P \cdot sum = \sum_{i=1}^{n} (1 + Pi \cdot \sigma i) \cdot |Pi \cdot SP|,$$

The present process value for the total power consumption of the other functional elements Fj is also determined. An individual dynamic reserve is taken into account here using the variation Fj.σ, i.e. in the case where Fj.σ>0:

$$F \cdot sum = \sum_{j=1}^{m} (1 + Fj \cdot \sigma j) \cdot |Fj \cdot PV|,$$

In this way, the individual power consumptions of the functional components Pi and/or of the other functional elements Fj can be dynamically altered, as an option, for example to take different operating situations into consideration.

The total power S.sum required in the present operating situation is determined:

$$S.\text{sum}=P.\text{sum}+F.\text{sum}$$

If S.sum is less than or equal to the currently available maximum output value of power supply S.max, all the functional elements Pi can be reliably provided with the required power:

$$\forall_i \text{Pi.SP'}=\text{Pi.SP}$$

However, if S.sum is greater than the currently available maximum output power of power supply S.max, then an appropriate strategy for distributing the available power among the functional elements Pi must be applied in order to maintain reliable operation. Alternative variants are available for this purpose.

In one variant, the total power P.sum' that can be distributed to the functional elements Pi is determined:

$$P.\text{sum}'=S.\text{max}-F.\text{sum}$$

One preferred embodiment endeavours to continue an existing relative distribution of power among the functional elements Pi. A reduction factor x is calculated for this purpose, which lies within the range $\alpha$ . . . 1:

$$x = \frac{P \cdot sum'}{P \cdot sum}$$

In a further step, the individual power setpoint values Pi.SP' are calculated as follows:

$$\forall_i \text{Pi.SP'}=x \cdot \text{Pi.SP}$$

The system as a whole is managed safely and reliably on the basis of these reduced power setpoint values.

The precondition for implementing the power control concept described above is that the functional elements Pi are amenable to at least one of the following kinds of control:

Elements are involved whose individual power consumption can be altered/adjusted.

Several elements with a constant (unchangeable) power consumption are involved, but these can be switched on and off either individually or in groups.

Controlled provision of power for the system or functional components may be carried out according to averaging all the components involved, such that each functional component is provided the same share of power. As an alternative or in addition thereto, the system components may be weighted when supplying power. For example, selected system components may be provided at all times with their maximum power requirement. Or such system components may be completely excluded from any shut-downs. A reduction in the supplied power may also be limited for such system components to a certain percentual amount, for example to 30% of the normal/maximum power consumption.

The proposed load management system can be realised for any combination of system or functional components of the bioreactor system. The above description for a particular embodiment was based on temperature control devices. Similarly, a common load management system may be provided, for example, for stirrers and/or temperature control devices which are assigned to a respective bioreactor in the bioreactor system.

The features of the invention which are disclosed in the above description, in the claims and in the drawings may be material in their various embodiments, both separately and in any combination, for realising the invention.

The invention claimed is:

1. A biotechnological apparatus comprising:
   a bioreactor,
   a reactor vessel formed in the bioreactor and having a cultivation chamber, and
   a temperature control device provided with a heat pump and configured to control the temperature of the cultivation chamber, wherein the heat pump is thermally coupled to the cultivation chamber via the reactor vessel and to a reference body forming a heat source potential for the heat pump and made of a heat-conducting material, and transfers heat, with supply of drive energy, from the reactor vessel to the reference body, or vice versa.

2. The apparatus according to claim 1, wherein the heat pump is a heat pump which can be driven by electrical drive energy.

3. The apparatus according to claim 1, wherein the reactor vessel is arranged in a vessel receptacle and the heat pump is thermally coupled to the reactor vessel via the vessel receptacle.

4. The apparatus according to claim 1, wherein the reference body is thermally coupled to an operating environment of the bioreactor.

5. The apparatus according to claim 4, wherein the reference body is thermally coupled to the operating environment of the bioreactor via an adjustable thermal resistance.

6. The apparatus according to claim 1, wherein the heat pump is coupled to a controller which is configured to control, during operation of the bioreactor, the supply of drive energy for transferring the heat from the reactor vessel to the reference body, or vice versa, in accordance with a predefined operational management scheme.

7. A bioreactor system comprising a plurality of biotechnological apparatuses, each comprising:
   a bioreactor,
   a reactor vessel formed in the bioreactor and having a cultivation chamber, and
   a temperature control device configured to control the temperature of the cultivation chamber and provided with a heat pump which is thermally coupled to the cultivation chamber via the reactor vessel and to a reference body made of a heat-conducting material, and transfers heat, with supply of drive energy, from the respective reactor vessel to the reference body, or vice versa,
   wherein the reference body forms a shared heat source potential for the heat pumps of the plurality of biotechnological apparatuses.

8. The apparatus according to claim 7, wherein the heat pump for at least one of the bioreactors is a heat pump which can be driven by electrical drive energy.

9. The apparatus according to claim 7, wherein the reactor vessel for at least one of the bioreactors is arranged in a vessel receptacle and the heat pump is thermally coupled to the reactor vessel via the vessel receptacle.

10. The apparatus according to claim 7, wherein the reference body for at least one of the bioreactors is thermally coupled to an operating environment of the bioreactor.

11. The apparatus according to claim 10, wherein the reference body is thermally coupled to the operating environment of the bioreactor via an adjustable thermal resistance.

12. The apparatus according to claim 7, wherein the heat pump for at least one of the bioreactors is coupled to a controller which is configured to control, during operation of the bioreactor, the supply of drive energy for transferring the heat from the reactor vessel to the reference body, or vice versa, in accordance with a predefined operational management scheme.

* * * * *